US012669512B2

(12) United States Patent
Saito et al.

(10) Patent No.: US 12,669,512 B2
(45) Date of Patent: Jun. 30, 2026

(54) PROTEIN DIAGNOSTIC BIOMARKER FOR SEVERE CUTANEOUS DRUG ADVERSE REACTIONS

(71) Applicants:JAPAN AS REPRESENTED BY DIRECTOR GENERAL OF NATIONAL INSTITUTE OF HEALTH SCIENCES, Kanagawa (JP); TOSOH CORPORATION, Yamaguchi (JP)

(72) Inventors: Yoshiro Saito, Kanagawa (JP); Ryosuke Nakamura, Kanagawa (JP); Noriaki Arakawa, Kanagawa (JP); Yasuo Ohno, Kanagawa (JP); Takashi Izumi, Kanagawa (JP); Motonobu Sato, Ibaraki (JP); Takayoshi Nishiya, Tokyo (JP); Michiko Aihara, Kanagawa (JP)

(73) Assignees: JAPAN AS REPRESENTED BY DIRECTOR GENERAL OF NATIONAL INSTITUTE OF HEALTH SCIENCES, Kanagawa (JP); TOSOH CORPORATION, Yamaguchi (JP)

( * ) Notice: Subject to any disclaimer, the term of this patent is extended or adjusted under 35 U.S.C. 154(b) by 827 days.

(21) Appl. No.: 17/918,449

(22) PCT Filed: Apr. 15, 2021

(86) PCT No.: PCT/JP2021/015613
§ 371 (c)(1),
(2) Date: Jan. 12, 2023

(87) PCT Pub. No.: WO2021/210651
PCT Pub. Date: Oct. 21, 2021

(65) Prior Publication Data
US 2023/0146286 A1     May 11, 2023

(30) Foreign Application Priority Data
Apr. 17, 2020    (JP) ................................. 2020-073955

(51) Int. Cl.
*G01N 33/68*      (2006.01)
*G01N 33/94*      (2006.01)

(52) U.S. Cl.
CPC ......... *G01N 33/6893* (2013.01); *G01N 33/94* (2013.01); *G01N 2800/50* (2013.01); *G01N 2800/56* (2013.01)

(58) Field of Classification Search
None
See application file for complete search history.

(56) References Cited

U.S. PATENT DOCUMENTS

| 2009/0068670 | A1 | 3/2009 | Georges et al. |
| 2014/0220580 | A1 | 8/2014 | Brown et al. |
| 2014/0286929 | A1 | 9/2014 | Kossen et al. |

FOREIGN PATENT DOCUMENTS

| JP | 2010-286375 A | 12/2010 |
| WO | 2019/202972 A1 | 10/2019 |

OTHER PUBLICATIONS

Chung WH, Hung SI, Yang JY, Su SC, Huang SP, Wei CY, Chin SW, Chiou CC, Chu SC, Ho HC, Yang CH, Lu CF, Wu JY, Liao YD, Chen YT. Granulysin is a key mediator for disseminated keratinocyte death in Stevens-Johnson syndrome and toxic epidermal necrolysis. Nat Med. Dec. 2008; 14(12):1343-50. (Year: 2008).*

(Continued)

*Primary Examiner* — Rebecca M Giere
*Assistant Examiner* — Alexander Alexandrovic Volkov
(74) *Attorney, Agent, or Firm* — Greenblum & Bernstein, P.L.C.

(57) ABSTRACT

Biomarkers for diagnosing the disease activity, disease severity or disease type of severe cutaneous adverse drug (Continued)

reactions (SCARs) such as drug-induced hypersensitivity syndrome and Stevens-Johnson syndrome/toxic epidermal necrolysis are provided. Also provided is a method of testing SCARs, comprising measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in a sample derived from a subject.

22 Claims, 2 Drawing Sheets

(56) References Cited

OTHER PUBLICATIONS

Osabe M, Tajika T, Tohkin M. Allopurinol suppresses expression of the regulatory T-cell migration factors TARC/CCL17 and MDC/CCL22 in HaCaT keratinocytes via restriction of nuclear factor-κB activation. J Appl Toxicol. Feb. 2018;38(2):274-283. (Year: 2018).*

Aihara et al., "Evaluation of serum cytokine levels in toxic epidermal necrolysis and Stevens-Johnson syndrome compared with other delayed-type adverse drug reactions", The Journal of Dermatology, 2011, pp. 1076-1079.

Hama et al., "Galectin-7 as a potential biomarker of Stevens-Johnson syndrome/toxic epidermal necrolysis: identification by targeted proteomics using causative drug-exposed peripheral blood cells", The Journal of Allergy and Clinical Immunology; In Practice, 2019, pp. 2894-2897.

Komatsu-Fujii et al., "The thymus and activation-regulated chemokine (TARC) level in serum at an early stage of drug eruption is a prognostic biomarker of severity of systemic inflammation", Allergology International, 2018, pp. 90-95.

International Search Report Issued in International Patent Application No. PCT/JP2021/015613, dated Jul. 6, 2021, along with an English translation thereof.

Office Action for CN App. No. 202180042679.9, dated Apr. 3, 2025 (w/ translation).

ESR for EP App. No. 21789239.7, dated Aug. 12, 2024.

Burch et al., "Chapter 10: Serious Drug Rashes in Children", Advances in Pediatrics, Year Book Medical Publishers, Chicago, IL, US, 52:207-222 (2005).

Stephan et al., "Lamotrigine-induced hypersensitivity syndrome with histologic features of cd30+ lymphoma", Indian Journal of Dermatology, 61:235 (2016).

Weingertner et al., "Intralymphatic CD30+ T-cell proliferation during DRESS: a mimic of intravascular lymphoma", Journal of Cutaneous Pathology, 43:1036-1040 (2016).

"Invitrogen User Guide: Human sCD30 Instant ELISA Kit", ThermoFischer Scientific, Pub. No. MAN0016617 Rev. A.0 (30), Aug. 20, 2019.

Pizzolo et al., "High serum level of soluble CD30 in acute primary HIV-1infection", Clinical and Experimental Immunology, 108:251-253 (1997).

Dummer et al., "Elevated serum levels of soluble CD30 are associated with atopic dermatitis, but not with respiratory atopic disorders and allergic contact dermatitis", British Journal of Dermatology, 137:185-187 (2003).

Duong et al., "Severe cutaneous adverse reactions to drugs", The Lancet, 390:1996-2011 (2017).

ESR for EP App. No. 21789239.7, dated Apr. 23, 2024.

Uno et al.: "TNF-[alpha] as a useful predictor of human herpesvirus-6 reactivation and indicator of the disease process in drug-induced hypersensitivity syndrome (DIHS)/drug reaction (DR) with eosinophilia and systemic symptoms (DRESS)", Journal of Dermatological Science, 74(2):177-179 (2014).

Watanabe, "Recent Advances in Drug-Induced Hypersensitivity Syndrome/ Drug Reaction with Eosinophilia and Systemic Symptoms", Journal of Immunology Research, vol. 2018, pp. 1-10 (2018).

Su et al., "Interleukin-15 Is Associated with Severity and Mortality in Stevens-Johnson Syndrome/Toxic Epidermal Necrolysis", Journal of Investigative Dermatology, 137(5):1065-1073 (2017).

Shiba-Ishii et al., "High expression of stratifin is a universal abnormality during the course of malignant progression of early-stage lung adenocarcinoma", International Journal of Cancer, 129(10):2445-2453 (2011).

Ryu et al., "Proteomic analysis of psoriatic skin tissue for identification of differentially expressed proteins: Up-regulation of GSTP1, SFN and PRDX2 in psoriatic skin", International Journal of Molecular Medicine, 28:785-792 (2011).

Search Report dated Nov. 4, 2025 in Chinese patent application No. 202180042679.9, with English machine translation thereof.

Office Action dated Nov. 8, 2025 in Chinese patent application No. 202180042679.9, with English machine translation thereof.

\* cited by examiner

[Fig. 1]
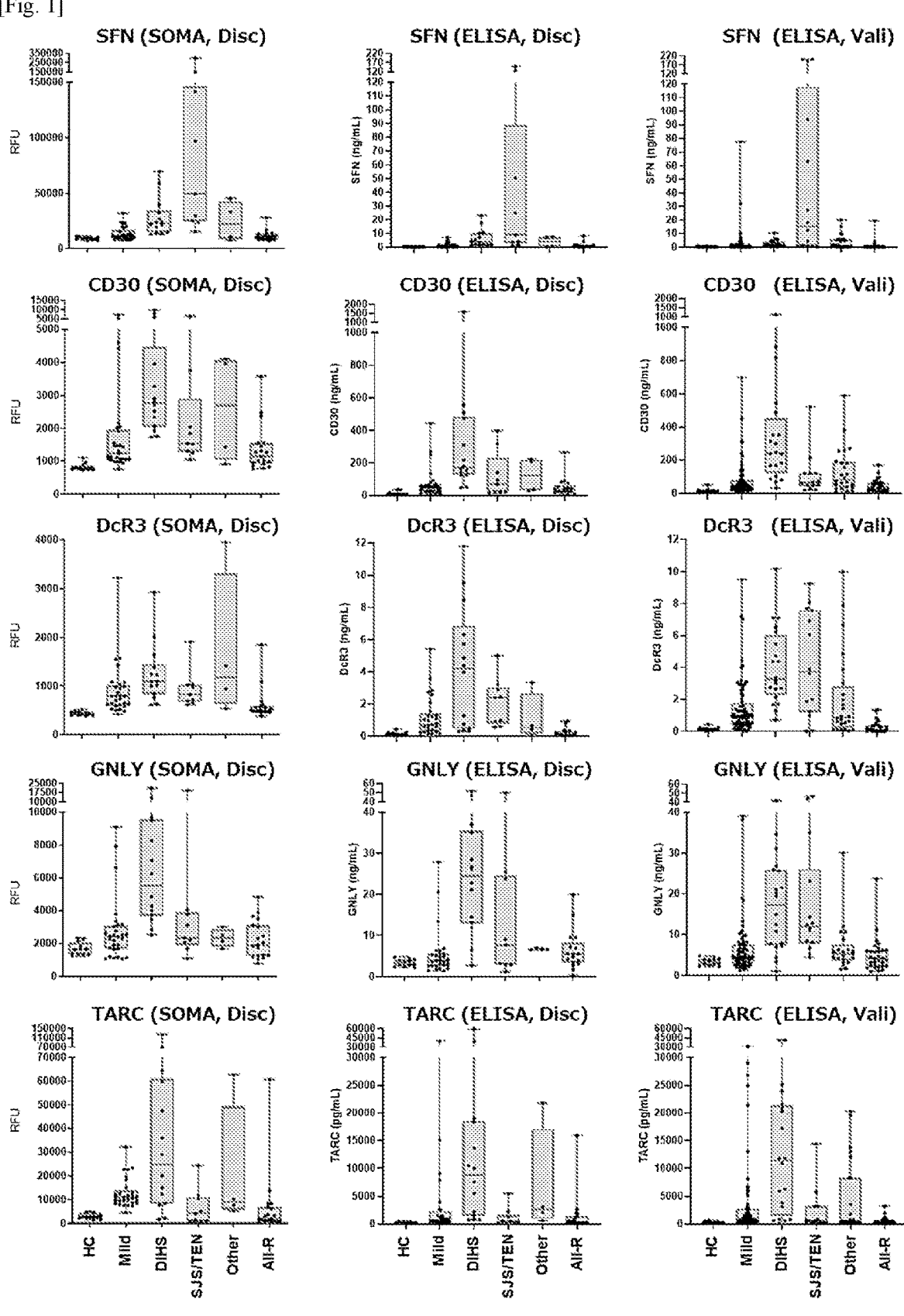

[Fig. 2]
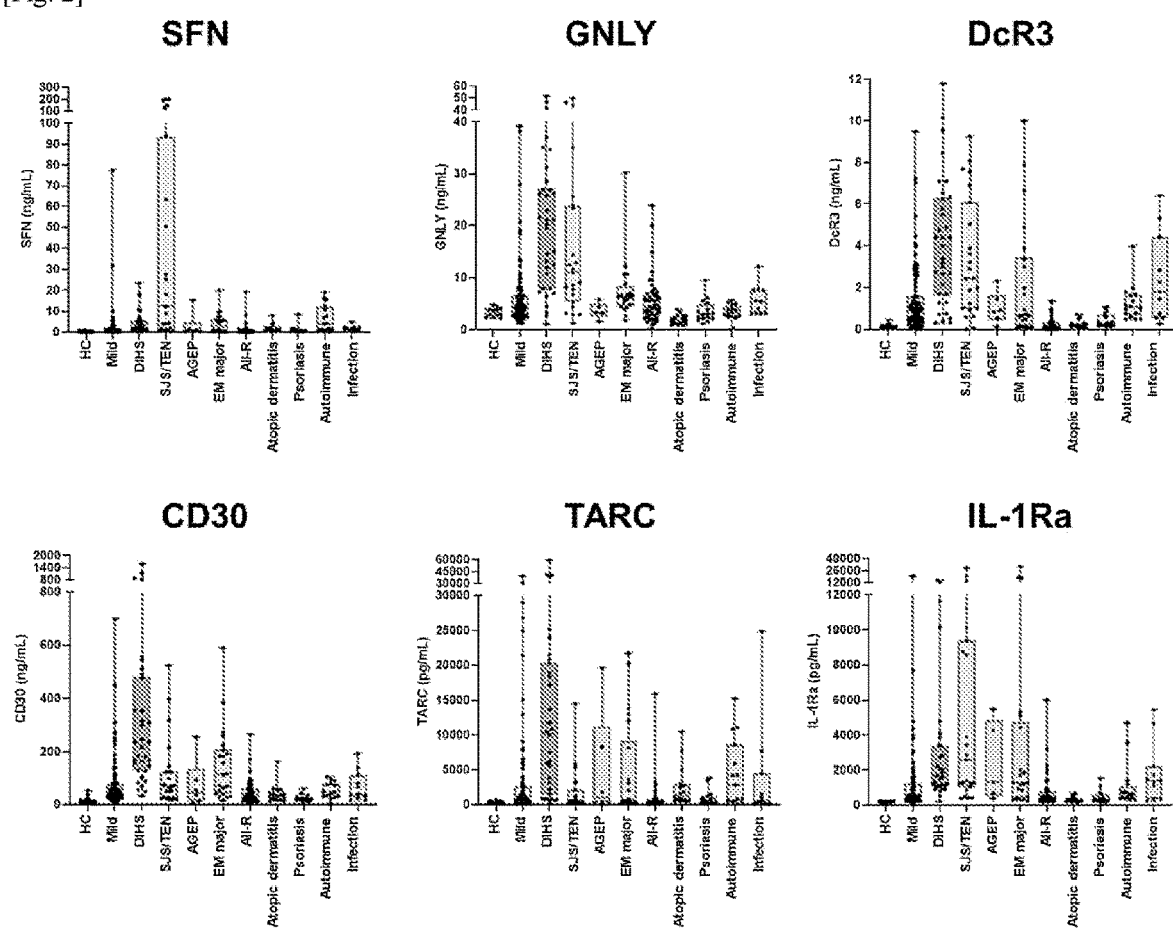

PROTEIN DIAGNOSTIC BIOMARKER FOR SEVERE CUTANEOUS DRUG ADVERSE REACTIONS

TECHNICAL FIELD

The present invention relates to a method for aiding the diagnosis of the onset or the disease activity of severe cutaneous adverse drug reactions (SCARs).

BACKGROUND ART

SCARS, including Stevens-Johnson syndrome (SJS), toxic epidermal necrolysis (TEN) and drug-induced hypersensitivity syndrome (DIHS), may leave serious aftereffects and often lead to death. Therefore, it is critical to diagnose at an early stage and to promptly start proper treatment. For this purpose, biomarkers for diagnosing DIHS or SJS/TEN at an early stage are needed.

To date, TARC (chemokine CCL17), granulysin (GNLY), FAS-L, interleukin 6 (IL-6), IP-10 (chemokine CXCL10) and combinations thereof have been proposed as protein markers in blood in SCARS, though necessity of sufficient validation was recognized (Non-Patent Documents Nos. 1-3).

Stratifin (SFN), also known as 14-3-3 sigma, is a 27-kDa protein. It is suggested that increase of the SFN expression in lung tissue is associated with oncogenic transformation (Non-Patent Document No. 4). In skin tissue, expression of the SFN gene is induced by UV exposure. Using this as an indicator, a technique to test the degree of skin damage is developed (Patent Document No. 1).

CD30 (TNFRSF8) is one member of the TNF receptor super-family and is a 120-kDa type I transmembrane protein. CD30 is expressed in activated lymphocytes in healthy persons. Among hematologic malignant tumors, CD30 is known to be expressed strongly in tumor cells of Hodgkin's lymphoma. Therefore, the CD30 test using a immunohistological technique has attracted attention as a useful method for diagnosing Hodgkin's lymphoma. Recently, expression of CD30 has been also confirmed in anaplastic large cell lymphoma and non-hematologic malignancy, and anti-CD30 antibody therapy or the like has been developed (Non-Patent Document No. 5).

However, until now, neither the fact that SFN and soluble CD30 in blood are able to detect SJS/TEN or DIHS, nor the effect thereof has been known. Further, with respect to interleukin-1 receptor antagonist (IL-1Ra) and TNF receptor superfamily member 6B (DcR3/TNFRSF6B), their association with the onset of SCARs has not also been known.

PRIOR ART LITERATURE

Non-Patent Documents

Non-Patent Document No. 1: Komatsu-Fujii T et al. The thymus and activation-regulated chemokine (TARC) level in serum at an early stage of a drug eruption is a prognostic biomarker of severity of systemic inflammation, Allergology Int. 67, 90-95, 2018

Non-Patent Document No. 2: Abe R, et al. Rapid immuno-chromatographic test for serum granulysin is useful for the prediction of Stevens-Johnson syndrome and toxic epidermal necrolysis. J Am Acad Dermatol. 2011, 65(1): 65-8.

Non-Patent Document No. 3: Shiohara T, et al. Monitoring the acute response in severe hypersensitivity reactions to drugs. Curr Opin Allergy Clin Immunol. 2015, 15(4):294-9.

Non-Patent Document No. 4: Shiba-Ishii A, Noguchi M. Aberrant stratifin overexpression is regulated by tumor-associated CpG demethylation in lung adenocarcinoma. Am J Pathol. 2012 April; 180(4):1653-62.

Non-Patent Document No. 5: Junichi Tamaru, CD30. Modern Media Vol. 60, No. 11, 2015 "Clinical Test Update", 323, 11-14

Patent Document

Patent Document No. 1: Japanese Unexamined Patent Publication No. 2012-39970

DISCLOSURE OF THE INVENTION

Problem for Solution by the Invention

The present invention aims at providing a method for aiding the diagnosis of Stevens-Johnson syndrome/toxic epidermal necrolysis (SJS/TEN) or drug-induced hypersensitivity syndrome (DIHS) with high accuracy; a method for objectively evaluating the efficacy of treatment of these reactions; and a method for aiding the discrimination between patients with mild drug eruption which will be cured without exacerbation and patients with drug eruption which will be exacerbated.

Means to Solve the Problem

The present inventors have searched for biomarker proteins which are considered to be useful for the diagnosis of disease activity or severity in Stevens-Johnson syndrome/ toxic epidermal necrolysis (SJS/TEN) or drug-induced hypersensitivity syndrome (DIHS), by a proteomic analysis of plasma samples from SCAR patients using SOMAscan™ assay. Briefly, based on the quantitative data on 1310 proteins, the present inventors searched for the proteins which exhibit remarkable changes in the acute phase of the patients with SCARS and identified the following four protein candidates, stratifin (SFN, 14-3-3 protein sigma), TNF receptor superfamily member 8 (CD30/TNFRSF8), interleukin-1 receptor antagonist (IL-1Ra) and TNF receptor superfamily member 6B (DcR3/TNFRSF6B), in addition to the known biomarker candidates, TARC (chemokine 17/CCL17) and granulysin (GNLY). The validation study by ELISA revealed that CD30 has the highest performances and is superior to known biomarkers, granulysin and TARC, in the diagnosis of the disease activity of DIHS (discrimination between patients in acute phase and in recovery phase) and in the determining severity of DIHS (discrimination from patients with mild drug eruption). Furthermore, in the diagnosis of disease activity or severity of SJS/TEN, SFN showed the most excellent biomarker performances. By combining these proteins, it was possible to improve the positivity rate of DIHS or SJS/TEN, or discrimination performance between SJS/TEN and DIHS, which require different therapeutic strategies. In particular, the SFN/TARC ratio was useful for the specific diagnosis of SJS/TEN (differential diagnosis from DIHS).

The present invention has been achieved based on these findings. A summary of the present invention is described as below.

(1) A method of testing SCARS, comprising measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in a sample derived from a subject.

(2) The method of (1) above, further comprising measurements of the expression for at least one protein selected from the group consisting of granulysin (GNLY) and C-C motif chemokine 17 (TARC/CCL17) in a sample derived from a subject.

(3) The method of (1) or (2) above, wherein the protein whose expression is to be measured is at least one protein selected from the group consisting of stratifin, TNF receptor superfamily member 8 (CD30/TN-FRSF8), interleukin-1 receptor antagonist (IL-1Ra) and TNF receptor superfamily member 6B (DcR3/TNFRSF6B), and the resultant measured values aid the diagnosis of severity of severe cutaneous adverse drug reactions.

(4) The method of (1) or (2) above, wherein the protein whose expression is to be measured is at least one protein selected from the group consisting of stratifin, TNF receptor superfamily member 8 (CD30/TN-FRSF8), interleukin-1 receptor antagonist (IL-1Ra) and TNF receptor superfamily member 6B (DcR3/TNFRSF6B), and the resultant measured values aid the diagnosis of disease activity of SCARs.

(5) The method of (1) or (2) above, wherein the protein whose expression is to be measured is stratifin, and the resultant measured values aid the diagnosis of drug-induced hypersensitivity syndrome and/or Stevens-Johnson syndrome/toxic epidermal necrolysis.

(6) The method of (1) or (2) above, wherein the protein whose expression is to be measured is TNF receptor superfamily member 8 (CD30/TNRSF8), and the resultant measured values aid the diagnosis of drug-induced hypersensitivity syndrome and/or Stevens-Johnson syndrome/toxic epidermal necrolysis.

(7) The method of (1) or (2) above, wherein the protein whose expression is to be measured is at least one combination of proteins selected from the group consisting of a combination of stratifin and C-C motif chemokine 17 (TARC/CCL17) and a combination of stratifin and TNF receptor superfamily member 8 (CD30/TNFRSF8), and the resultant measured values aid the specific diagnosis of drug-induced hypersensitivity syndrome and/or Stevens-Johnson syndrome/toxic epidermal necrolysis.

(8) A method of diagnosing SCARs, comprising:
   a3. obtaining a sample from a subject;
   b3. measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject; and
   c3. assessing the severity of drug eruption based on the measured values from b3.

(9) A method of diagnosing SCARs, comprising:
   a2. obtaining a sample from a subject;
   b2. measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject; and
   c2. determining the disease activity of SCARS based on the measured values from b2.

(10) A method of diagnosing SCARs, comprising:
   a4. obtaining a sample from a subject;
   b4. measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFR-SF6B) in the sample from the subject; and
   c4. judging the disease type of SCARs based on the measured values from b4.

(11) A method of diagnosing and treating SCARS, comprising:
   a3. obtaining a sample from a subject;
   b3. measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject;
   c3. assessing the severity of drug eruption based on the measured values from b3; and
   d3. stopping the administration of the suspected drug which has been administered to the subject, and starting an appropriate treatment according to the severity of the drug eruption, if it is judged that the subject is highly likely to develop or to have developed SCARs.

(12) A method of diagnosing and treating SCARS, comprising:
   a2. obtaining a sample from a subject;
   b2. measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject;
   c2. determining the disease activity of SCARs based on the measured values from b2; and
   d2. stopping the administration of the suspected drug which has been administered to the subject, and starting an appropriate treatment, if it is judged that the subject is highly likely to be in an acute phase.

(13) A method of diagnosing and treating SCARS, comprising:
   a4. obtaining a sample from a subject;
   b4. measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject;
   c4. judging the disease type of SCARs based on the measured values from b4; and
   d4. stopping the administration of the suspected drug which has been administered to the subject, and starting an appropriate treatment according to the disease type of SCARs.

(14) A kit for testing SCARs, comprising a reagent capable of measuring the expression of at least one protein selected from the group consisting of stratifin, TNF receptor superfamily member 8 (CD30/TN-FRSF8), interleukin-1 receptor antagonist (IL-1Ra), and TNF receptor superfamily member 6B (DcR3/TNFRSF6B) in a sample derived from a subject.

Effect of the Invention

It is considered most critical to initiate the treatment of SCARs as early as possible. The proteins which the present inventors have found can be novel blood biomarkers for discriminating severe patients with DIHS or SJS/TEN from patients with mild drug eruption (severity diagnosis biomarker). Further, those proteins can be useful biomarkers for the diagnosis of disease activity, for example, judging whether a patient with DIHS or SJS/TEN has experienced a transition to a recovery phase (disease activity diagnosis biomarker). Still further, these proteins can be useful markers for judging whether the disease type of a patient is DIHS or SJS/TEN (disease type diagnosis biomarker). In particular, stratifin and CD30 showed a higher accuracy compared to the existing biomarker candidates, TARC and granulysin. By combining stratifin or CD30 with existing TARC or granulysin, early detection and specific diagnosis of DIHS or SJS/TEN patients will become possible.

The present specification encompasses the contents disclosed in the specification and/or the drawings of Japanese Patent Application No. 2020-73955 based on which the present application claims priority.

BRIEF DESCRIPTION OF THE DRAWINGS

FIG. 1 Results of SOMAscan™ assay performed in the biomarker discovery study and results of validation study by ELISA. Disc: Discovery-set (sample set for biomarker discovery study); Vali: Validation-set (sample set for validation study); HC: healthy control; Mild: mild drug eruption; DIHS: DIHS in acute phase; SJS/TEN: SJS/TEN in acute phase; Other: other SCARs in acute phase (acute generalized exanthematous pustulosis and erythema multiforme major); All-R: all SCAR patients in recovery phase.

FIG. 2 Distributions of blood concentrations of each biomarkers in healthy normals, patients with mild drug eruption, SCARs and various skin diseases. Results of measurement on the Combined-set are shown. HC: healthy controls; Mild: mild drug eruption; DIHS: DIHS in acute phase; SJS/TEN: SJS/TEN in acute phase; AGEP: acute generalized exanthematous pustulosis in acute phase; EM-major: erythema multiforme major in acute phase; All-R: recovery phase groups; Atopic dermatitis: atopic dermatitis; Psoriasis: psoriasis; Autoimmune: autoimmune bullous disease; Infection: infectious skin diseases.

BEST MODES FOR CARRYING OUT THE INVENTION

Hereinbelow, embodiments of the present invention will be described in detail.

The present invention provides a method of testing SCARs, comprising measurement of the expression for at least one protein selected from the group consisting of stratifin, TNF receptor superfamily member 8 (CD30/TN-FRSF8), interleukin-1 receptor antagonist (IL-1Ra), and TNF receptor superfamily member 6B (DcR3/TNFRSF6B) in a sample derived from a subject.

Drug eruption is a rash occurring in response to drugs and is a type of adverse reaction. Generally, the onset of drug eruption is 1 to 2 weeks after beginning a new medicament. Since withdrawal of the causative drug ameliorates drug eruption, diagnosis is easy. However, SCARS is not ameliorated in many cases by withdrawal of the causative drug alone and can be life-threatening without appropriate treatment. Therefore, early diagnosis is critical.

Stevens-Johnson syndrome (SJS) and toxic epidermal necrolysis (TEN), which are representative type of SCARs, are refractory diseases that have a high fatality and leave aftereffects such as blindness or respiratory disorders. SJS and TEN are considered pathological conditions of the same disease spectrum. The symptoms of TEN resemble those of SJS but are more severe, and in many cases TEN progresses from SJS. SJS symptoms include extensive mucosal lesions in the mucocutaneous junctions, such as the lip, conjunctiva and vulva, accompanied by fever. SJS is characterized by erosions and blisters based on epidermal necrotic disorders along with widespread erythemas on the skin. The area of such erosions and blisters is less than 10% of the body surface. On the other hand, TEN exhibits widespread erythemas, and remarkable epidermal necrotic disorders (such as blisters, skin detachment or eruptions) involving 10% or more of the body surface, along with high fever and enanthem. TEN is considered the most severe dermal disorder caused by pharmaceutical products. Incidences of SJS and TEN are annually 1 to 6 persons per million and 0.4 to 1.3 persons per million, respectively.

Alongside SJS/TEN, drug-induced hypersensitivity syndrome (DIHS) is also a disease type of SCARS. Erythematous papules and erythema multiforme accompanied by a high fever of 38° C. or more are observed all over the body, and may progress to erythroderma. Enanthem is usually absent or mild, but oral mucosal erosions are occasionally observed. Systemic lymphadenopathy, organ disorder including liver dysfunction, and peripheral leukocyte abnormalities (leukocytosis, eosinophilia, and emergence of atypical lymphocytes) are observed. It is characteristic to DIHS that reactivation of human herpesvirus (HHV)-6 occurs during the course. When lymphadenopathy or reactivation of HHV-6 is not proved, the DIHS is diagnosed as "atypical DIHS". Different from ordinary drug eruption, DIHS does not onset immediately after administration of the causative drugs, but after two weeks or more in many cases. Symptoms remain even after withdrawal of the causative drugs, and often require one month or more for amelioration.

Although it is considered critical to diagnose these SCARs early and to promptly start appropriate treatment, early discrimination or prediction of those patients whose condition would be exacerbated is difficult because initial symptoms patients with SCARs resemble those of patients with mild drug eruption. Further, for treating exacerbated patients, it is also critical to know the disease type of the patients early and to assess the disease activity (activity of the condition) appropriately.

To date, TARC (chemokine CCL17) known as a severity assessment biomarker for atopic dermatitis has been proposed for validation of DIHS; or granulysin and Fas ligands, etc. have been proposed as blood protein markers in SCARs for detection of SJS/TEN.

Stratifin, also known as 14-3-3 sigma, is a protein of 248 amino acids encoded by SFN gene. It is known that stratifin is expressed in the epithelium of esophagus and skin and that the expression thereof is increased in head and neck cancer, pulmonary cancer, cervical cancer and the like. In the epidermis of skin, the expression of stratifin is increased by UV in a p53-dependent manner. Stratifin is thought to affect fibroblast cells in the dermis so as to be involved in wound healing and the regulation of fibrogenesis. The UniProt number of SFN is P31947.

TNF receptor superfamily member 8 (CD30/TNFRSF8) is a type I transmembrane protein of 593 amino acids encoded by TNFRSF8 gene belonging to the TNF receptor family. In healthy normal adults, the expression of CD30 is only recognized in activated T and B cells. However, in Hodgkin's lymphoma, CD30 is strongly expressed in mononuclear Hodgkin cells, multinucleated Reed-Sternberg cells, anaplastic large cell lymphoma, and the like. CD30 causes activation of NFκB via phosphorylation of IκB and is involved not only in the secretion of cytokines but also in the regulation of inflammation as well as in the survival and proliferation of cells. In clinical tests, cellular immunity test is performed using CD30 as a marker for adult T-cell leukemia, Hodgkin's lymphoma, and Ki-1 lymphoma. It has been reported that soluble CD30 is released upon cleavage by binding of CD30L and elevated under conditions of oxidative stress. The UniProt number is P28098.

Interleukin-1 receptor antagonist (IL-1Ra) is an extracellular secretion protein of 159 amino acids encoded by IL1RN gene. This protein binds to receptor IL-1R1 and inhibits the activation of interleukin-1α and -1β. This protein is expressed highly in cells of the bone marrow and the immune system, as well as in cells of the gastrointestinal tract. It is known that this protein is involved in the modulation of skin aging in skin tissues. The UniProt number is P18510.

TNF receptor superfamily member 6B (DcR3/TNFRSF6B) is registered with its formal designation being TNF receptor superfamily member 6B, and is a protein of 245 amino acids encoded by TNFRSF6 gene. This protein is known as a decoy receptor belonging to the TNF receptor family. This protein has an effect of inhibiting Fas-induced apoptosis signal by binding to Fas ligand as a decoy receptor. It is known that plasma DcR3 is elevated in rheumatoid arthritis patients. The UniProt number is O95407.

Stratifin, CD30, IL-1Ra, and DcR3/TNFRSF6B are novel and yet useful as biomarkers for SCARS.

In the method of the present invention, preferably, the protein whose expression is to be measured is stratifin, and the measured values aid the diagnosis of drug-induced hypersensitivity syndrome (DIHS) and/or Stevens-Johnson syndrome/toxic epidermal necrolysis (SJS/TEN). Diagnosis includes diagnosis of disease activity, diagnosis of severity, specific diagnosis of disease type, and so forth.

Alternatively, in the method of the present invention, preferably, the protein whose expression is to be measured is CD30, and the measured values aid the diagnosis of DIHS and/or SJS/TEN. Diagnosis includes diagnosis of disease activity, diagnosis of severity, specific diagnosis of disease type, and so forth.

In one embodiment of the method of the present invention, expression of known blood protein markers for SCARs (such as granulysin (GNLY), TARC, etc.) may further be measured in a sample derived from a subject. By combining novel markers or combining novel marker(s) and known marker(s), positivity rate of SCARs may be improved and specificity may be increased.

In the method of the present invention, the subject is a mammal which is suspected to have developed SCARs, but any mammal that is considered to be at the risk of developing SCARS may be included in the subject. Typically, the subject is human. As samples derived from the subject, cells, tissues, and body fluids obtained from the subject may be used. Specific examples include, but are not limited to, the subject's blood (e.g., whole blood, serum, plasma, external fluid from plasma exchange, etc.) and bronchoalveolar lavage fluid. Whole blood, serum or plasma obtained from routine blood tests (clinical tests) may be used conveniently as a blood sample.

In the method of the present invention, the measurement of expression in a sample from the subject may consist of measuring the amount of the above-described protein or a fragment thereof contained in the sample. Means of measurement is not particularly limited and known methods may be used. Measurement at the protein level is preferred but measurement may also be performed at the nucleic acid level.

In order to measure the expression of the above-described protein at the protein level, antibodies which specifically recognize the above-described protein may be conveniently used. The antibody may be either monoclonal or polyclonal. These antibodies may be prepared by known methods, or commercially available products may be used. As a typical method, an immunoassay such as ELISA or immunochromatography may be given. Since immunoassays do not require special equipment or technique and are capable of easily and promptly detect and quantify a target protein, immunoassays may be used preferably in the method of the present invention for measuring the above-described proteins. Antibodies to the above-described proteins are known and commercial products are also available. Further, as described above, the amino acid sequences of the above-described proteins and nucleotide sequences encoding those sequences are also known. Therefore, specific antibodies to individual proteins may be produced by preparing common hybridomas.

Immunoassays per se are well known in this area. Immunoassays include the sandwich method, the competitive method, the agglutination method, Western blotting and the like depending on the reaction format; and enzyme immunoassay, radioimmunoassay, fluorescence immunoassay, luminescence immunoassay and the like based on the label.

Any immunoassay that allows quantitative detection may be used in the present invention. Although not particularly limited, a sandwich method such as sandwich ELISA may, for example, be preferably used. In the sandwich method, an antibody that binds to a target protein is immobilized and reacted with a sample. The target protein bound to the immobilized antibody is measured using a detection antibody labeled with an enzyme or the like. As the detection antibody, it is preferable to use an antibody that binds to the target protein at a site different from the binding site of the immobilized antibody. The immobilized antibody and the detection antibody may be either polyclonal antibodies or monoclonal antibodies, and antigen-binding fragments of these antibodies may also be used. The target protein bound to the immobilized antibody is reacted with the detection antibody, and washed. Then, the amount of the bound detection antibody is measured with signals from the substance labeling the antibody. For example, when an antibody labeled with alkaline phosphatase is used as a detection antibody, the substrate of the enzyme is added to the reaction system, and the amount of color development, fluorescence, or luminescence generated by the enzyme reaction may be measured with an appropriate device. Immunoassay is performed on target protein-containing standard samples of known concentrations; and a calibration curve is prepared in advance by plotting the relationship between the signal from the labeling substance and the protein concentration. Then, the same operation is performed on a sample containing the target protein at unknown concentration. The target protein in the sample can be quantified by applying the resultant signal values to the calibration curve.

For measuring the expression of the above-described protein at the nucleic acid level, a nucleic acid probe capable of specifically hybridizing to the mRNA of the above-described protein may be conveniently used (when the expression is to be measured by Northern blotting). Alternatively, at least one pair of nucleic acid primers capable of specifically amplifying the cDNA synthesized using the mRNA of the above-described protein as a template may be used (when the expression is to be measured by RT-PCR). The nucleic acid probe and the nucleic acid primers may be designed based on the genetic information (as described above) of the above-described protein. Usually, nucleic acid probes may suitably be about 15 to 500 bases in length. Nucleic acid probes may be labeled with radioactive elements, fluorescent dyes, enzymes and the like. Usually, nucleic acid primers may suitably be about 15 to 30 bases in length. Nucleic acid primers may be labeled with radioactive elements, fluorescent dyes, enzymes, and the like.

The number of the proteins or genes whose expression is to be measured may be either one or multiple. More accurate evaluation may become possible by referring to expression data of multiple genes or proteins. In order to detect expression of multiple genes or proteins simultaneously, detection methods such as DNA array (in which probes are immobilized on a substrate) (Nature Reviews, Drug Discovery, Volume 1, December 2002, 951-960), protein chip (in which antibodies are immobilized on a substrate) (Nature Reviews, Drug Discovery, Volume 1, September 2002, 683-695), Luminex™ assay (Nature Reviews, Drug Discovery, Volume 1, June 2002, 447-456) or the like may be used.

Specific examples of combinations of proteins or genes whose expression is to be measured include, but are not limited to, the combinations and ratios disclosed in Table 10 in the Example described later (CD30+TARC, CD30+SFN, CD30+GNLY, CD30+IL-1Ra, SFN/TARC ratio, and SFN/CD30 ratio).

It is possible to determine the disease activity of SCARs, assess severity of SCARs, or judge the disease type of SCARS by measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in a sample derived from a subject, and making a determination, assessment or judgment based on the resultant expression level.

Therefore, the method of the present invention is capable of aiding the diagnosis of SCARs (diagnosis of disease activity, diagnosis of disease severity, and specific diagnosis of disease type).

As one exemplary case of the present invention, the diagnosis of SCARs may be performed on the following criterion. First, the expression of at least one of the above-listed proteins in plasma sampled from a subject is measured. When the resultant value is higher than a pre-determined cut-off value or reference value, it is determined that the subject has developed SCARs. The pre-determined cut-off value may be appropriately set by one of ordinary skill in this area. For example, 95% confidence interval of the quantified values of healthy persons who have not developed SCARs may be set as the reference value, or the cut-off value may be set from ROC curve. Alternatively, when at least one of the above-listed proteins shows a tendency of elevation compared to the values of measurement in the past, the subject is suspected of possible development of SCARs. The cut-off values of respective biomarker candidates as shown in Tables 5 to 8 in the Example described later were set by analyzing the ROC curves in comparing DIHS or SJS/TEN at acute phase and control groups (all of recovery phase groups, mild symptom groups, or various skin disease groups) and referring to Youden Index (sensitivity+specificity−100).

The method of the present invention may be used for diagnosing the severity of SCARs. As used herein, "diagnosis of severity" means discriminating SCARs such as SJS/TEN or DIHS from mild drug eruption such as disseminated erythematous papular rash or erythema multiforme. When the expression level of at least one protein selected from the group consisting of stratifin, CD30, IL-1Ra, and DcR3 in a sample derived from a subject is high, it is possible to judge that the subject is highly likely to develop SCARS in the future or to have developed SCARs already.

Cut-off values for discriminating DIHS or SJS/TEN from mild drug eruption may be set at various levels, for example, 2 to 8 ng/ml (preferably 3.7 ng/ml) for stratifin, 1.5 to 3 ng/ml (preferably 2.6 ng/ml) for DcR3, 1000 to 2000 pg/ml (preferably 1600 pg/ml) for IL-1Ra, or 50 to 150 ng/ml (preferably 82 ng/ml) for CD30.

The present invention provides a method of diagnosing SCARs, comprising:

a3. obtaining a sample from a subject;

b3. measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject; and c3. assessing the severity of drug eruption based on the measured values from b3.

Further, the present invention may be used for determining disease activity of SCARs. As used herein, "diagnosis of disease activity" means discriminating the acute phase of SCARs such as SJS/TEN or DIHS from the recovery phase thereof. When the expression level of at least one protein selected from the group consisting of stratifin, CD30, IL-1Ra, and DcR3 in a sample derived from a subject is high, it is possible to judge that the subject is highly likely to be in the acute phase of SCARs.

Cut-off values for diagnosing the disease activity of DIHS or SJS/TEN may be set at various levels, for example, 1 to 3 ng/ml (preferably 1.0 ng/ml) for stratifin, 0.3 to 2 ng/ml (preferably 1.1 ng/ml) for DcR3, 500 to 1500 pg/ml (preferably 930 pg/ml) for IL-1Ra, or 50 to 150 ng/ml (preferably 100 ng/ml) for CD30.

The present invention provides a method of diagnosing SCARs, comprising:

a2. obtaining a sample from a subject;

b2. measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject; and c2. determining the disease activity of SCARs based on the measured values from b2.

SFN has high ability to detect SJS/TEN in particular, and CD30 to detect DIHS in particular. DcR3 and IL-1Ra have an ability to a detect both SJS/TEN and DIHS.

Furthermore, the present invention may be used for specific diagnosis of SCARS. As used herein, "specific diagnosis" means judging the disease type of SCARS. Since SCARS such as SJS/TEN or DIHS may leave serious aftereffects or even lead to death, it is clinically very significant that the present invention is applicable to specific diagnosis of SCARS. For example, when the expression level of stratifin in a sample derived from a subject is high, it is possible to judge that the disease type of the subject is very likely to be SJS/TEN. Further, when the expression level of CD30 in a sample derived from a subject is high, it is possible to judge that the disease type of SCARs of the subject is very likely to be DIHS. In order to improve the detection rate of SCARs, biomarkers may be combined. For example, a combination of stratifin and TARC is capable of improving the performance for judging SJS/TEN. For judging SJS/TEN, SFN/TARC ratio may be conveniently used. Further, combinations of CD30 and TARC; CD30 and stratifin; CD30 and granulysin (GNLY); and CD30 and IL-1Ra are capable of improving the performance for detecting DIHS.

Cut-off values for specific diagnosis of SJS/TEN may be set at various levels, for example, 3 to 7 ng/ml (preferably 4.3 ng/ml) for stratifin. As a cut-off value for specific diagnosis of DIHS, various levels may be set, for example, 60 to 240 ng/ml (preferably 124 ng/ml) for CD30, 1 to 3 ng/ml (preferably 2.6 ng/ml) for DcR3, or 1000 to 4000 pg/ml (preferably 2040 pg/ml) for IL-1Ra. In order to improve the performance for detecting DIHS or SJS/TEN, individual markers having these cut-off values may also be used in combination. Further, combination with a known marker TARC (exemplary cut-off value: 5500 pg/ml) or GNLY (exemplary cut-off value: 10.7 ng/ml) can also improve the performance for detecting DIHS or SJS/TEN. The cut-off value of SFN/TARC ratio for improving the performance for judging SJS/TEN may be set at 4 to 7 (preferably 5.6).

The present invention provides a method of diagnosing SCARs, comprising:

a4. obtaining a sample from a subject;

b4. measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject; and c4. judging the disease type of SCARs based on the measured values from b4.

The method of the present invention for diagnosis of the disease activity of SCARs may also be used in tests for prediction of prognosis and judging therapeutic efficacy. For example, if it is determined that a subject is highly likely in the exacerbated acute phase of SCARs, expression of at least one protein selected from the group consisting of stratifin, CD30, IL-1Ra and DcR3 in a sample derived from the subject is measured once or more than once at different times. When the expression level has decreased to a level close to a cut-off value or a reference value, it is possible to judge that the subject has recovered from the SCARs by treatment. When the expression level is high or does not decrease, it is possible to judge that the subject has not recovered from the SCARs by treatment or the recovery of the subject is insufficient. Regarding a cut-off value for determining recovery by treatment, the cut-off value for diagnosing disease activity is effective.

When it is determined that the subject is highly likely to develop or to have developed SCARs already, administration of the suspected causal drug is stopped and an appropriate therapy is initiated according to the disease activity of the subject and individual symptoms of the disease type. As drug therapy for DIHS, systemic steroid administration (starting from a dose of 0.5 to 1 mg/kg/day of prednisolone which is gradually reduced in an appropriate manner) is effective. The dose should be reduced with care taken to avoid the relapse of symptoms from reactivation of HHV-6. For SJS/TEN, a recommended regimen is systemic steroid administration using different doses depending on the severity (starting from a dose of 0.5 to 1 mg/kg/day for mild cases and 1 to 2 mg/kg/day for severe cases of prednisolone for both cases; and starting from a dose of 1 g of methyl prednisolone/day×3 days for most severe cases. These doses are gradually reduced in an appropriate manner depending on the symptoms). In addition to the above, high dose human immunoglobulin (IVIG) intravenous infusion therapy (administration at a dose of 400 mg/kg/day for 5 consecutive days; in principle, one course only), plasma exchange, conservation of ocular surface epithelium by preventing symblepharon, infection prophylaxis on ocular surface, or reduction of ocular surface inflammation caused by eye disorder which can be treated with instillation of betamethasone or dexamethasone (about 4 times/day), etc. may also be recommended.

SCARs is also a major adverse effect in the United States. As regards SJS/TEN, the Genetic and Rare Diseases Information Center (GARD) established by funding from National Institutes of Health (NIH) discloses symptoms, causes, therapies and prognosis (rarediseases.info.nih.gov/diseases/7700/stevens-johnson-syndrometoxic-epidermalnecrolysis). As treatment of SJS/TEN, necessity of hospitalization and withdrawal of drugs administered, as well as supportive therapy and drug therapy are enumerated. In supportive therapy, generally, treatment of skin manifestations is similar to treatment of severe burns and includes wound care, pain management, body fluids and electrolytes, nutrition support, body temperature management, and monitoring or treatment of secondary infections. As regards treatment of eye manifestations, washing with normal saline is mentioned. As regards drug therapy, systemic corticosteroid, intravenous immunoglobulin (IVIG), cyclosporine, plasma exchange, and anti-tumor necrosis factor (TNF) monoclonal antibody are enumerated, but it is stated that none of these have been sufficiently studied by randomized trial. As regards drug therapy for eyes, lubrication of eyes with preservative-free eye drops or ointment for multiple times a day, and treatment with ophthalmic medicines containing topical corticosteroids and broad-spectrum antibiotics are enumerated. In a survey made at 22 university hospitals and reported in 2018, among 377 SJS/TEN patients, 29.3% received supportive therapy alone, 30.0% received steroid alone, 24.9% received IVIG therapy, and 14.3% received both steroid and IVIG therapy (Michaeletti R G et al., J Invest Dermatol., 2018; 138:2315-2321).

As regards DIHS (also known as Drug Reaction with Eosinophilia and Systemic Symptoms: DRESS), GARD also discloses symptoms and clinical researches, but describes nothing about therapies (rarediseases.info.nih.gov/diseases/13629/drug-reaction-with-eosinophilia-and-systemic-symptoms). According to an analysis report using the computerized medical information of Partners HealthCare System Inc. in Boston, among 3,162,562 patients, 69 cases had DRESS and 51 cases received corticosteroid. Of them, 35 cases received topical steroid; 36 cases received oral steroid; and 26 cases received intravenous steroid (Wolfson A R et al., J Allergy Clin Immunol Pract., 2019; 7:633-640).

The present invention provides a method of diagnosing and treating SCARS, comprising:

a3. obtaining a sample from a subject;

b3. measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject;

c3. assessing the severity of SCARs based on the measured values from b3; and d3. stopping the administration of the suspected drug which has been administered to the subject, and starting an appropriate treatment according to the severity of the drug eruption, if it is judged that the subject is highly likely to develop or to have developed SCARs.

Further, the present invention provides a method of diagnosing and treating SCARs, comprising:

a2. obtaining a sample from a subject;

b2. measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject;

c2. determining the disease activity of SCARs based on the measured values from b2; and d2. stopping the administration of the suspected drug which has been administered to the subject, and starting an appropriate treatment, if it is determined that the subject is highly likely to be in an acute phase.

Still further, the present invention provides a method of diagnosing and treating SCARs, comprising:

a4. obtaining a sample from a subject;

b4. measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject;

c4. judging the disease type of SCARs based on the measured values from b4; and d4. stopping the administration of the suspected drug which has been administered to the subject, and starting an appropriate treatment according to the disease type of SCARS.

The present invention also provides a kit for testing SCARS, comprising a reagent capable of measuring the expression of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in a sample derived from a subject.

As one example, the kit of the present invention comprises as a reagent an antibody capable of specifically recognizing the above-described protein. The antibody may be immobilized on microtiter plates, magnetic beads, cellulose membranes or substrates. The kit may further comprise instruments for collecting samples from subjects, anti-coagulants, a set of reagents for detecting the above-described protein, instructions, etc. The instructions may conveniently include not only description on how to use the kit but also description on the criteria for determination of exacerbated acute phase of SCARS, assessing the severity of drug eruption and/or judgment of disease type.

As another example, the kit of the present invention comprises as a reagent a nucleic acid probe capable of specifically hybridizing with an mRNA of the above-described protein. The nucleic acid probe may be immobilized on a substrate. The kit may further comprise instruments for collecting biosamples, anti-coagulants, reagents for extracting RNA from samples derived from the subjects, reagents for detecting RNA, instructions, etc. The handling instructions may conveniently include not only description on how to use the kit but also description on the criteria for determination of exacerbated acute phase of SCARs, assessing the severity of drug eruption and/or judgment of disease type.

As still another example, the kit of the present invention comprises as a reagent at least one pair of nucleic acid primers capable of specifically amplifying a cDNA synthesized using the mRNA of the above-descried protein as a template. The kit may further comprise instruments for collecting samples from subjects, anti-coagulants, reagents for extracting RNA from samples derived from the subjects, reagents for detecting RNA, instructions, etc. The handling instructions may conveniently include not only description on how to use the kit but also description on the criteria for determination of exacerbated acute phase of SCARS, assessing the severity of drug eruption and/or judgment of disease type.

The kit of the present invention may further comprise standard proteins, buffers, substrates (when antibodies are enzyme-labeled), reaction stop solutions, washing solutions, reaction vessels, and so on.

The kit of the present invention for diagnosis of SCARs is also capable of diagnosing SJS caused by infections such as mycoplasma infection. The kit of the present invention may be used as a pharmaceutical for diagnosing diseases.

EXAMPLES

Hereinbelow, the present invention will be described in detail with reference to the following Example.

Example 1

(1) Samples

Blood (plasma and serum) samples from patients with drug eruptions were collected after obtaining approval from Research Ethics Review Committees in participating five hub hospitals, the National Institute of Health Sciences, the Kihara Foundation, Astellas Pharma Inc., and Daiichi Sankyo Company. In five hub hospitals, Yokohama City University, Shimane University, Shimada Municipal Hospital/Iwata City Hospital, Nara Medical University, and Niigata University, blood samples were collected from those patients who were suspected to have developed mild drug eruption (erythema multiforme, maculopapular exanthema, or eczematous rash) and patients with related skin diseases. Blood samples were also collected from patients with skin diseases other than drug eruption (atopic dermatitis, psoriasis, autoimmune bullous disease, infectious skin diseases (excluding measles, rubella and varicella). These samples (plasma and serum) were cryopreserved at −80° C. As regards samples from healthy persons, those collected in NEUES Co., Ltd. were used.

The particulars of the samples are shown in Table 1. Seventy-five samples from patients who developed diseases and 12 samples from healthy persons as collected by the end of November, 2017 were used for searching by SOMAscan™-based analysis and analytical validation of ELISA kits (Discovery set, Table 1). Next, as a sample group independent from "Discovery set", which were collected in or after December, 2017 (163 samples from patients who developed diseases, and 38 samples from healthy controls not used in the discovery study) were used for validation of biomarkers (Validation-set). Further, Discovery-set, Validation-set, and samples from related diseases were combined to make "Combined set", with which evaluation of diagnostic performances of each biomarker was performed.

Table 1. Particulars of the Samples Used for Analysis

TABLE 1

| Particulars of the Samples used for Analysis | | | |
|---|---|---|---|
| Disease | Discovery set SOMA, ELISA | Validation set ELISA | Combined-set ELISA |
| Total (n) | 87 | 201 | 260 |
| Healthy group | 12 | 38 | 38 |
| Mild drug eruption | 29 | 76 | 76 |
| DIHS    Acute phase | 14 | 20 | 20 |
| Recovery phase | 10 | 11 | 11 |
| SJS/TEN    Acute phase | | | |
| Recovery phase | | | |
| AGEP    Acute phase | 0 | 6 | 6 |
| Recovery phase | 0 | 2 | 2 |
| EM-major    Acute phase | 4 | 18 | 18 |
| Recovery phase | 2 | 7 | 7 |
| All of recovery phase groups | 19 | 27 | 27 |
| Atopic dermatitis | — | — | 16 |
| Psoriasis | — | — | 16 |
| Autoimmune bullous disease | — | — | 16 |
| Infectious skin diseases | — | — | 11 |

(2) Screening of Biomarker Candidates

Biomarker candidates for SJS/TEN and DIETS, which are considered particularly important disease types in clinical practice, were searched by a proteome analysis using SOMAscan™ system that can detect 1,310 proteins with aptamers (artificial ligands of single stranded nucleic acid). Frozen plasma samples of Discovery set were sent to SomaLogic Inc. in the United States and subjected to SOMAscan™ assay.

Based on the measured values of 1,310 proteins obtained by SOMAscan™ assay, the present inventors searched for (1) biomarker candidates for determination of the disease activity for DIHS or SJS/TEN (comparison between acute phase and recovery phase) and (2) severe symptom-related biomarker candidates for discriminating DIHS or SJS/TEN from mild symptom group (comparison of SCAR patient group in acute phase and mild symptom group). After logarithmic transformation of the measured value (relative fluoresce intensity) for each probe of SOMAscan, the data were compared between the mild drug eruption (Mild, N=29), acute phase of DIHS (DIHS, n=14), acute phase of SJS/TEN (SJS/TEN, n=9), all recovered SCAR patients (All-R, n=19), and healthy controls (HC, n=12). Then, the present inventors focused on the proteins that increased in either DIHS or SJS/TEN in acute phase compared to the All-R or Mild groups, with the following criteria: effect size [Hedge's g value] and/or fold change [FC] fell within the top 10, and AUC values of ROC curve of 0.85 and more. This analysis revealed that stratifin, CD30, DcR3 and IL-1Ra (did not known to be useful as the biomarkers for SCARs), as well as known biomarkers TARC and granulysin (GNLY), were fit the above criteria. Table 2 shows these biomarker candidates and ELISA kits used in the validation study.

Table 2. Biomarker Candidate Proteins and ELISA Kits
Used for the Validation Study.

TABLE 2

| Biomarker Candidate Proteins and ELISA kits used for the Validation Study. | | | |
|---|---|---|---|
| Biomarker candidate | Uniprot ID | ELISA Kit | Matrix |
| Stratifin (SFN) | P31947 | In-house ELISA | Serum |
| CD30/TNFRSF8 | P28908 | Invitrogen | Serum |
| DcR3/TNFRSF6B | O95407 | R&D Systems DuoSet ™ | Plasma |
| IL-1Ra | P18510 | R&D Systems Quantikine ™ | Plasma |
| Granulysin (GNLY) [known] | P22749 | In-house ELISA | Serum |
| TARC/CCL17 [known] | Q92583 | Sysmex Corporation, HISCL TARC | Serum |

(3) Comparison of Measurement Values

FIG. 1 shows the change patterns of the blood levels of 6 biomarker candidates measured using SOMAscan™ and ELISA. In SOMAscan™ analysis, all protein candidates showed a marked increase in each disease type of SCAR compared to the healthy and Mild groups, and decreased in the recovered patients to a level close to that of healthy control group. Similar results were also obtained in ELISA. Moreover, the concentration ranges in the healthy control group, DIHS or SJS/TEN patients, and recovery patients in the Discovery and Validation-sets were similar (FIG. 1).

(4) Utility in Diagnosis of Disease Activity and Severity 4-1) Analysis with the Discovery-Set Table 3 shows the comparison data of the diagnostic performances for assessment of disease activity (discrimination between acute phase and recovery phase in SCAR patients) and severity of patients (discrimination between the SCAR group and the Mild group) for DIHS or SJS/TEN based on AUC values calculated from ROC curve analysis in the Discovery-set. SFN, DcR3, and IL-1Ra were suggested to have a high diagnostic performance for both DIHS and SJS/TEN; and SFN showed a particularly high performance for detection of SJS/TEN. In contrast, CD30 showed high performance for detection of DIHS. The performances for assessment of disease activity (AUC 0.93) and severity (AUC 0.87) in CD30 were higher than those of known biomarker TARC (AUC 0.89 and 0.82, respectively).

Table 3. Comparison of AUC Values on the Diagnostic Performance for Assessment of Disease Activity and Severity of DIHS and SJS/TEN (Discovery-Set)

Numerical values 0.85 or more shown in bold letters.

4-2) Analysis with the Validation-Set

Table 4 shows the results of ROC analysis in the Validation-set. In the Validation-set, SFN showed a high diagnostic performance especially for SJS/TEN; CD30 showed a high diagnostic performance for DIHS; and DcR3 and IL-1Ra showed a diagnostic performance for both DIHS and SJS/TEN, in line with data of the Discovery-set. In terms of the performances for determination and assessments of disease activity and severity for DIHS, DcR3 (AUC 0.99 and 0.86) and CD30 (AUC 0.94 and 0.89) were superior to known biomarkers TARC (AUC 0.91 and 0.78) and GNLY (AUC 0.86 and 0.81). For SJS/TEN, SFN showed the highest value (AUC 0.92) in determination of the disease activity. Although the diagnostic performance of SFN for determination of disease severity of SJS/TEN was slightly lowered in the Validation-set (AUC 0.79) compared to the data obtained in the Discovery-set (AUC 0.91, Table 3), SFN showed the highest value (AUC 0.84) in the Combined-set (with combined data from the Discovery and Validation-sets) (Table 4). IL-1Ra (AUC 0.80) followed SFN, showing a higher value than known biomarker GNLY (AUC 0.76) (Table 4).

TABLE 3

| | Discovery set (SOMAscan) | | | | Discovery set (ELISA) | | | |
|---|---|---|---|---|---|---|---|---|
| | DIHS (n = 14) | | SJS/TEN (n = 9) | | DIHS (n = 14) | | SJS/TEN (n = 9) | |
| Candidate | vs All-R Disease activity | vs Mild Severity | vs All-R Disease activity | vs Mild Severity | vs All-R Disease activity | vs Mild Severity | vs All-R Disease activity | vs Mild Severity |
| SFN | 0.93 | 0.88 | 0.98 | 0.96 | 0.89 | 0.86 | 0.94 | 0.91 |
| DcR3 | 0.92 | 0.75 | 0.89 | 0.60 | 0.94 | 0.74 | 0.97 | 0.72 |
| IL-1Ra | 0.86 | 0.82 | 0.79 | 0.75 | 0.90 | 0.88 | 0.81 | 0.83 |
| CD30 | 0.93 | 0.86 | 0.75 | 0.67 | 0.93 | 0.87 | 0.60 | 0.56 |
| GNLY [known] | 0.93 | 0.89 | 0.66 | 0.57 | 0.88 | 0.91 | 0.57 | 0.64 |
| TARC [known] | 0.87 | 0.77 | 0.56 | 0.58 | 0.89 | 0.82 | 0.56 | 0.61 |

Numerical values 0.85 or more are shown in bold letters.

Table 4. Comparison of AUC Values on the Diagnostic Performance for Assessment of Disease Activity and Severity for DIHS and SJS/TEN (Validation-Set)

TABLE 4

Comparison of AUC Values on the Diagnostic Performance for Assessment of Disease Activity and Severetiy for DIHS and SJS/TEN (Validation-set)

| | Validation set (ELISA) | | | |
| | DIHS (n = 20) | | SJS/TEN (n = 14) | |
| | | | vs All-R | |
| Candidate | vs All-R Disease activity | vs Mild Severity | Disease activity | vs Mild Severity |
| --- | --- | --- | --- | --- |
| SFN | 0.84 | 0.69 | 0.92 | 0.79 |
| DcR3 | 0.99 | 0.86 | 0.89 | 0.75 |
| IL-1Ra | 0.85 | 0.76 | 0.89 | 0.81 |
| CD30 | 0.94 | 0.89 | 0.72 | 0.62 |
| GNLY [known] | 0.86 | 0.81 | 0.90 | 0.85 |
| TARC [known] | 0.91 | 0.78 | 0.61 | 0.62 |

Numerical values 0.85 or more are shown in bold letters.

4-3) Analysis with the Combined-Set
4-3-1) Disease Specificity

Using the data of the Combined-set, distributions of measured values of respective candidate proteins were compared in various skin diseases including drug eruption (FIG. 2). Any of the candidate proteins showed a marked elevation in DIHS and/or SJS/TEN. In particular, SFN was elevated characteristically in SJS/TEN but showed only a moderate increase in other diseases including DIHS and EM-major, or in autoimmune bullous skin disease. On the other hand, CD30 showed a DIHS-specific elevation, as well as TARC, and a slight increase in part of EM-major, but there was little increase in autoimmune bullous skin disease. DcR3 and GNLY showed a tendency of increasing in both DIHS and SJS/TEN, unlike SFN and CD30.

4-3-2) Determination of Disease Activity in DIHS and SJS/TEN

Table 5 shows the results of analysis using the Combined-set, showing the performances of respective candidate proteins for determination of the disease activity of DIHS and SJS/TEN. The present inventors set cut-off values for discriminating between the patients with DIHS or SJS/TEN in acute phase and all SCAR patients in recovery phase (All-R), and compared their sensitivies and specificities. In the determination of the disease activity for DIHS, DcR3 (AUC 0.96) and CD30 (AUC 0.94) were effective. When the cut-off value of DcR3 was set at 1.1 ng/ml, and that of CD30 was set at 100 ng/ml, either of the proteins discriminated the acute DIHS patients from all recovered patients with a sensitivity of more than 80% and a specificity of more than 90%. DcR3 and SFN showed good performances for determinating the disease activity of SJS/TEN (AUC value was 0.9 or more for both diseases). When the cut-off value of DcR3 was set at 0.55 ng/ml, the protein discriminated the acute phase patients with SJS/TEN from all recovered patients with a sensitivity of more than 90% and a specificity of more than 85%. When the cut-off value of SFN was set at 1.0 ng/ml, this protein discriminated the acute phase patients with SJS/TEN from all recovered patietns with both sensitivity and specificity being more than 80%.

Table 5. Cut-Off Values and Diagnostic Performances for Determination of the Disease Activity of DIHS and SJS/TEN (Combined-Set)

TABLE 5

Cut-off Values and Diagnostic Performances for Determination of the Disease Activity of DIHS and SJS/TEN (Combined-set)

| | Combined set (ELISA) | | | | | | | |
| | Determination of the disease activity in DIHS DIHS (n = 34) vs All-R | | | | Determination of the disease activity in SJS/TEN SJS/TEN (n = 23) vs All-R | | | |
| Candidate | AUC | Cut-off | Sencitivity | Specificity | AUC | Cut-off | Sencitivity | Specificity |
| --- | --- | --- | --- | --- | --- | --- | --- | --- |
| SFN | 0.84 | 1.1 ng/mL | 82.4% | 81.6% | 0.90 | 1.0 ng/mL | 82.6% | 81.6% |
| DcR3 | 0.96 | 1.1 ng/mL | 82.4% | 95.8% | 0.91 | 0.55 ng/mL | 91.3% | 85.4% |
| IL-1Ra | 0.87 | 930 pg/mL | 84.4% | 81.3% | 0.86 | 1000 pg/mL | 78.3% | 83.3% |
| CD30 | 0.94 | 100 ng/mL | 82.4% | 93.8% | 0.69 | — | — | — |
| GNLY [known] | 0.87 | 10 ng/mL | 73.5% | 91.7% | 0.77 | 7.5 ng/mL | 69.6% | 83.3% |
| TARC [known] | 0.91 | 3100 pg/mL | 70.6% | 95.9% | 0.59 | — | — | — |

Numerical values 0.85 or more are shown in bold letters.

Based on the results of ROC curve analysis in comparison between the DIHS and SJS/TEN patient in acute phase and all SCAR patients in recovery phase (All-R), the present inventors set as a cut-off value the concentration which would give the highest Youden Index with a specificity of more than 80%. AUC values of 0.85 or more are shown in bold letters. As for proteins having low discriminative performance (AUC≤0.7), cut-off values were not evaluated.

4-3-3) Assessment of Disease Severity in DIHS and SJS/TEN

Table 6 shows the results of analysis of the data of Combined-set, showing the performances of respective candidate proteins for assessment of severity in DIHS and SJS/TEN. The present inventors set cut-off values for discriminating the acute phase of DIHS and SJS/TEN from mild drug eruption group (Mild), and compared their sensitivities and specificities. In the assessment of severity in DIHS, CD30 (AUC 0.88) was the most excellent and superior to known biomarkers GNLY (AUC 0.85) and TARC (AUC 0.79). When the cut-off value of CD30 was set at 82 ng/ml, both sensitivity and specificity were more than 80% (Table 6). On the other hand, in the assessment of severity in SJS/TEN, SFN (AUC 0.84) was most excellent. When the cut-off value of SFN was set at 3.7 ng/ml, this protein discriminated the acute phase of SJS/TEN from mild drug eruption group with a sensitivity of about 70% and a specificity of about 90%.

Table 6. Cut-Off Values and Diagnostic Performances for Assessment of Severity in DIHS and SJS/TEN (Combined-Set)

ng/ml, both sensitivity and specificity were about 80%. In terms of specific diagnosis for SJS/TEN, SFN was the highest (AUC 0.79). When the cut-off value of SFN was set

TABLE 6

Cut-off Values and Diagnostic Performances for Assessment of Severity in DIHS and SJS/TEN (Combined-set)

| | Combined set (ELISA) | | | | | | | |
| | Assessment of Severity in DIHS DIHS (n = 34) vs Mild | | | | Assessment of Severity in SJS/TEN SJS/TEN (n = 23) vs Mild | | | |
| | AUC | Cut-off | Sencitivity | Specificity | AUC | Cut-off | Sensitivity | Specificity |
|---|---|---|---|---|---|---|---|---|
| SFN | 0.75 | 2.1 ng/mL | 50.0% | 80.0% | 0.84 | 3.7 ng/mL | 69.6% | 89.5% |
| DcR3 | 0.80 | 2.6 ng/mL | 67.7% | 83.8% | 0.73 | 2.4 ng/mL | 56.5% | 81.0% |
| IL-1Ra | 0.80 | 1600 pg/mL | 53.1% | 83.7% | 0.80 | 2500 pg/mL | 52.2% | 90.8% |
| CD30 | 0.88 | 82 ng/mL | 88.2% | 80.0% | 0.59 | — | — | — |
| GNLY [known] | 0.85 | 10 ng/mL | 73.5% | 89.1% | 0.76 | 7.7 ng/mL | 69.6% | 81.5% |
| TARC [known] | 0.79 | 3100 pg/mL | 70.6% | 81.7% | 0.63 | — | — | — |

Based on the results of ROC curve analysis in comparison between the acute phase of DIHS and SJS/TEN and mild drug eruption group, the present inventors set as a cut-off value the concentration which would give the highest Youden Index with a specificity of more than 80%. AUC at 4.3 ng/ml, diagnostic sensitivity and specificity were 60.9% and 81.8%, respectively.

Table 7. Cut-Off Values and Diagnostic Performances for Diagnosis of DIHS and SJS/TEN

TABLE 7

Cut-off Values and Diagnostic performances for Specific Diagnosis of DIHS and SJS/TEN

| | Combined set (ELISA) | | | | | | | |
| | Specific diagnosis of DIHS DIHS (n = 34) vs various skin diseases | | | | Specific diagnosis of SJS/TEN SJS/TEN (n = 23) vs various skin diseases | | | |
| Candidate | AUC | Cut-off | Sensitivity | Specificity | AUC | Cut-off | Sensitivity | Specificity |
|---|---|---|---|---|---|---|---|---|
| SFN | 0.67 | — | — | — | 0.79 | 4.3 ng/mL | 60.9% | 81.8% |
| DcR3 | 0.79 | 2.6 ng/mL | 67.7% | 80.8% | 0.72 | 2.9 ng/mL | 43.5% | 83.1% |
| IL-1Ra | 0.74 | 2040 pg/mL | 43.8% | 81.8% | 0.75 | 2500 pg/mL | 52.2% | 85.5% |
| CD30 | 0.87 | 124 ng/mL | 79.1% | 82.6% | 0.54 | — | — | — |
| GNLY [known] | 0.84 | 10.7 ng/mL | 73.5% | 87.2% | 0.73 | 10.9 ng/mL | 52.2% | 82.9% |
| TARC [known] | 0.80 | 5500 pg/mL | 64.7% | 83.4% | 0.65 | — | — | — | values 0.8 or more with sensitivity or specificity of 80% or more are shown in bold letters. As for proteins having low discriminative performance (AUC≤0.7), cut-off values were not evaluated.

4-3-4) Specific Diagnosis of Disease Types of SCARs

SJS/TEN and DIHS are particularly severer disease types among SCARs. Since these disease types require different therapeutic strategies, it is important to make a differential diagnosis of SJS/TEN or DIHS at an early stage. Hence, the present inventors compared the performances of respective proteins for detecting DIHS from among various skin diseases (DIHS-specific diagnostic performance) and their performances for detecting SJS/TEN specifically (SJS/TEN-specific diagnostic performance).

Cut-off values suitable for specific diagnosis of DIHS and SJS/TEN were set based on comparison between DIHS and skin diseases other than DIHS (including mild drug eruption, SCARs other than DIHS, and other skin diseases) and between SJS/TEN and skin diseases other than SJS/TEN (including mild drug eruption, SCARS other than SJS/TEN, and other skin diseases). Table 7 shows the results in comparison of their sensitivities and specificities. In terms of specific diagnosis for DIHS, CD30 was most excellent (AUC 0.87). When the cut-off value of CD30 was set at 124

Based on the ROC curve analysis in comparison between DIHS and skin diseases other than DIHS (including mild drug eruption, SCARs other than DIHS, and other skin diseases) and between SJS/TEN and skin diseases other than SJS/TEN (including mild drug eruption, SCARs other than SJS/TEN, and other skin diseases), the present inventors set as a cut-off value the concentration which would give the highest Youden Index with a specificity of more than 80%. AUC values 0.8 or more with sensitivity or specificity of 80% or more are shown in bold letters. As for proteins having low discriminative performance (AUC≤0.7), cut-off values were not evaluated.

Although SFN showed a SJS/TEN specificity, its sensitivity in specific diagnosis was 60.9%, a somewhat low value (Table 7). Hence, focusing on CD30 and TARC whose elevation in SJS/TEN was rather slight, the present inventors examined whether combination of SFN with these proteins would increase the performance for specific diagnosis of SJS/TEN. While the performance of SFN alone for specific diagnosis of SJS/TEN was AUC 0.79 (Table 7), AUC value was increased to 0.87 when the ratio to TARC value was used (SFN/TARC ratio). When the SFN/TARC ratio of 5.6 was used as a cut-off value, sensitivity was improved to more than 70% and specificity to more than 87%. Thus, this cut-off value was found to be capable of discriminating SJS/TEN from other skin diseases with high accuracy (Table 8).

TABLE 8

Improvement of the SJS/TEN-Specific Diagnostic Performance
by Combination of SFN and TARC

| | Combined set (ELISA) Specific Diagnosis of SJS/TEN SJS/TEN (n = 23) vs various skin diseases | | | |
|---|---|---|---|---|
| Candidate | AUC | Cut-off | Sensitivity | Specificity |
| SFN/TARC ratio | 0.87 | 5.6 | 73.9% | 87.8% |
| SFN/CD30 ratio | 0.71 | 71 | 60.8% | 86.2% |

Based on the results of ROC curve analysis of comparison between SJS/TEN and skin diseases other than SJS/TEN (including mild drug eruption, SCARs other than SJS/TEN, and other skin diseases), the present inventors have set as a cut-off value the concentration which would give the highest Youden Index with a specificity of more than 80%.

4-3-5) Comparison of Positivity Rates in Various Skin Diseases

Table 9 shows positivity rates in various skin diseases as obtained by using the cut-off values set in Table 7. Although SFN showed the highest positivity rate (61%) in SJS/TEN, positive cases were found even in EM-major (45%) and autoimmune bullous disease (47%). CD30 is a candidate protein with the highest positivity rate (79%) for DIHS and, unlike TARC, CD30 had no positive case in autoimmune bullous disease. DcR3 and GNLY showed a high positivity rate in both DIHS and SJS/TEN, unlike SFN and CD30.

Table 9. Comparison of Positivity Rates of Respective Biomarker Candidates in Various Skin Diseases Each positivity rate was calculated using, for SFN, the cut-off value for specific diagnosis of SJS/TEN and, for other proteins, the cut-off values for specific diagnosis of DIHS (Table 7). Positivity rates 50% or more are shown in bold letters. HC: healthy; Mild: mild drug eruption; DIHS: DIHS acute phase; SJS/TEN: SJS/TEN acute phase; AGEP: acute generalized exanthematous pustulosis; EM-major: erythema multiforme major: Atopic: atopic dermatitis; Psoriasis: psoriasis; Autoimmune: autoimmune bullous skin disease; Infection: infectious skin diseases.

Table 10 shows the results of comparison of the positivity rates of combined biomarkers. When positive was defined as both or either one of biomarkers in each combination above cut-off values, combination of CD30 and TARC improved the positivity rate for DIHS to more than 90%; and combination of CD30 and GNLY, and combination of CD30 and IL-1Ra also improved the positivity rate up to 85%. Furthermore, the positivity rate for SJS/TEN was highest when SFN/TARC ratio was used (positivity rate: 74%). These results indicated the utility of using the biomarker candidate proteins in combination.

TABLE 9

Comparison of Positivity Rates of Respective Biomarker Candidates in Various Skin Diseases

| | %, Positivity rate (N, positive samples/N, analyzed samples) Samples | | | | | |
|---|---|---|---|---|---|---|
| | SFN | DcR3 | IL-1Ra | CD30 | TARC | GNLY |
| | | | Positive | | | |
| | >4.3 ng/mL | >2.6 ng/mL | >2040 pg/mL | >124 ng/mL | >5500 pg/mL | >10.4 ng/mL |
| HC | 0 (0/50) | 0 (0/15) | 0 (0/16) | 0 (0/50) | 0 (0/24) | 0 (0/12) |
| Mild | 10 (10/105) | 17 (18/105) | 12 (12/97) | 15 (16/105) | 15 (16/104) | 11 (10/92) |
| DIHE | 29 (10/34) | 68 (23/34) | 44 (14/32) | 79 (27/34) | 62 (21/34) | 74 (25/34) |
| SJS/TEN | 61 (14/23) | 48 (11/23) | 52 (12/23) | 22 (5/23) | 9 (2/23) | 52 (12/23) |
| AGEP | 17 (1/6) | 0 (0/6) | 40 (2/5) | 17 (1/6) | 33 (2/6) | 0 (0/5) |
| EM-major | 45 (10/22) | 32 (7/22) | 29 (6/21) | 45 (10/22) | 27 (6/22) | 20 (4/20) |
| All-R | 4 (2/49) | 0 (0/48) | 8 (4/48) | 4 (2/48) | 2 (1/49) | 8 (4/48) |
| Atopic | 6 (1/16) | 0 (0/16) | 0 (0/16) | 6 (1/16) | 13 (2/16) | 0 (0/16) |
| Psoriasis | 6 (1/16) | 0 (0/16) | 0 (0/16) | 0 (0/16) | 0 (0/16) | 0 (0/16) |
| Autoimmune | 47 (7/15) | 6 (1/16) | 13 (2/16) | 0 (0/15) | 33 (5/15) | 0 (0/16) |
| Infection | 9 (1/11) | 36 (4/11) | 27 (3/11) | 18 (2/11) | 18 (2/11) | 9 (1/11) |

Table 10. Improvement of Positivity Rates for SCARS by Combination of Biomarker Candidates

TABLE 10

| Improvement of Positivity Rates for SCARs by Combination of Biomarker Candidates | | | | | |
|---|---|---|---|---|---|
| | %, Positivity rate (N, positive samples/N, analyzed samples) | | | | |
| Samples | CD30 + TARC | CD30 + SFN | CD30 + GNLY | CD30 + IL-1Ra | SFN/TARC |
| Positive | CD30 >124 (pg/mL), or TARC >5500 (pg/mL) | CD30 >124 (pg/mL), or SFN >4.3 (ng/mL) | CD30 >124 (pg/mL), or GNLY >10.4 (ng/mL) | CD30 >124 (pg/mL), or IL-1Ra >2040(pg/mL) | >5.6 |
| HC | 0 (0/24) | 0 (0/50) | 0 (0/12) | 0 (0/15) | 0 (0/24) |
| Mild | 25 (26/104) | 21 (22/105) | 18 (17/92) | 23 (22/97) | 8 (8/104) |
| DIHS | 91 (31/34) | 82 (28/34) | 85 (29/34) | 88 (28/32) | 9 (3/34) |
| SJS/TEN | 26 (6/23) | 70 (16/23) | 52 (12/23) | 61 (14/23) | 74 (17/23) |
| AGEP | 33 (2/6) | 33 (2/6) | 20 (1/5) | 60 (3/5) | 17 (1/6) |
| EM-major | 50 (11/22) | 64 (14/22) | 50 (10/20) | 48 (10/21) | 32 (7/22) |
| All-R | 4 (2/48) | 6 (3/48) | 10 (5/48) | 13 (6/47) | 12 (6/49) |
| Atopic | 13 (2/16) | 6 (1/16) | 6 (1/16) | 6 (1/16) | 0 (0/16) |
| Psoriasis | 0 (0/16) | 6 (1/16) | 0 (0/16) | 0 (0/16) | 6 (1/16) |
| Autoimmune | 33 (5/15) | 47 (7/15) | 0 (0/15) | 13 (2/15) | 20 (3/15) |
| Infection | 27 (3/11) | 18 (2/11) | 18 (2/11) | 45 (5/11) | 36 (4/11) |

Positivity rates were evaluated using, for SFN, the cut-off value for specific diagnosis of SJS/TEN and, for other proteins, the cut-off values for specific diagnosis of DIHS. Positivity rates 60% or more are shown in bold letters. HC: healthy; Mild: mild drug eruption; DIHS: DIHS acute phase; SJS/TEN: SJS/TEN acute phase; AGEP: acute generalized exanthematous pustulosis; EM-major: erythema multiforme major: Atopic: atopic dermatitis; Psoriasis: psoriasis; Auto-immune: autoimmune bullous disease; Infection: infectious skin diseases.

All publications, patents and patent applications cited herein are incorporated herein by reference in their entirety.

INDUSTRIAL APPLICABILITY

The present invention is applicable to in vitro diagnostics, clinical tests, and so on.

The invention claimed is:

1. A method of diagnosing and treating severe cutaneous adverse drug reactions, comprising:
   a. obtaining a sample from a subject;
   b. measuring an expression value of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject;
   c. assessing a severity of drug eruption based on the measured expression value of the at least one protein from b; and
   d. in the case it is determined from c that the subject is highly likely to develop or has developed severe cutaneous adverse drug reactions, stopping an administration of a suspect drug which was being administered to the subject, and starting an appropriate treatment according to the severity of the drug eruption assessed in c, and
      wherein the appropriate treatment is at least one selected from the group consisting of systemic corticosteroid treatment, intravenous immunoglobulin (IVIG) treatment, cyclosporine treatment, plasma exchange treatment, and anti-tumor necrosis factor (TNF) monoclonal antibody treatment.

2. The method of claim 1, further comprising measuring an expression value of at least one protein selected from the group consisting of granulysin (GNLY) and C-C motif chemokine 17 (TARC/CCL17) in the sample from the subject.

3. A method of diagnosing and treating severe cutaneous adverse drug reactions, comprising:
   a. obtaining a sample from a subject;
   b. measuring an expression value of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject;
   c. determining a disease activity of severe cutaneous adverse drug reactions based on the measured expression value of the at least one protein from b; and
   d. if it is determined in c that the subject is highly likely to be in an acute phase, stopping an administration of a suspect drug which was being administered to the subject, and starting an appropriate treatment, and
      wherein the appropriate treatment is at least one selected from the group consisting of systemic corticosteroid treatment, intravenous immunoglobulin (IVIG) treatment, cyclosporine treatment, plasma exchange treatment, and anti-tumor necrosis factor (TNF) monoclonal antibody treatment.

4. The method of claim 3, further comprising measuring an expression value of at least one protein selected from the group consisting of granulysin (GNLY) and C-C motif chemokine 17 (TARC/CCL17) in the sample from the subject.

5. A method of diagnosing and treating severe cutaneous adverse drug reactions, comprising:
   a. obtaining a sample from a subject;
   b. measuring an expression value of at least one protein selected from the group consisting of stratifin, TNF receptor superfamily member 8 (CD30/TNFRSF8), interleukin-1 receptor antagonist (IL-1Ra), and TNF receptor superfamily member 6B (DcR3/TNFRSF6B) in the sample from the subject;
   c. determining a disease type of severe cutaneous adverse drug reactions based on the measured expression value of the at least one protein from b; and d. stopping an administration of a suspect drug which was being administered to the subject, and starting an appropriate treatment according to the disease type of severe cutaneous adverse drug reactions determined in c, and wherein the appropriate treatment is at least one selected from the group consisting of systemic corticosteroid treatment, intravenous immunoglobulin (IVIG) treatment, cyclosporine treatment, plasma exchange treatment, and anti-tumor necrosis factor (TNF) monoclonal antibody treatment.

6. The method of claim 5, further comprising measuring an expression value of at least one protein selected from the group consisting of granulysin (GNLY) and C-C motif chemokine 17 (TARC/CCL17) in the sample from the subject.

7. The method of claim 5, wherein the protein whose expression value is to be measured is at least one combination of proteins selected from the group consisting of a combination of stratifin and C-C motif chemokine 17 (TARC/CCL17) and a combination of stratifin and TNF receptor superfamily member 8 (CD30/TNFRSF8).

8. The method according to claim 1, wherein the appropriate treatment is systemic corticosteroid treatment.

9. The method according to claim 1, wherein the appropriate treatment is intravenous immunoglobulin (IVIG) treatment.

10. The method according to claim 1, wherein the appropriate treatment is cyclosporine treatment.

11. The method according to claim 1, wherein the appropriate treatment is plasma exchange treatment.

12. The method according to claim 1, wherein the appropriate treatment is anti-tumor necrosis factor (TNF) monoclonal antibody treatment.

13. The method according to claim 3, wherein the appropriate treatment is systemic corticosteroid treatment.

14. The method according to claim 3, wherein the appropriate treatment is intravenous immunoglobulin (IVIG) treatment.

15. The method according to claim 3, wherein the appropriate treatment is cyclosporine treatment.

16. The method according to claim 3, wherein the appropriate treatment is plasma exchange treatment.

17. The method according to claim 3, wherein the appropriate treatment is anti-tumor necrosis factor (TNF) monoclonal antibody treatment.

18. The method according to claim 5, wherein the appropriate treatment is systemic corticosteroid treatment.

19. The method according to claim 5, wherein the appropriate treatment is intravenous immunoglobulin (IVIG) treatment.

20. The method according to claim 5, wherein the appropriate treatment is cyclosporine treatment.

21. The method according to claim 5, wherein the appropriate treatment is plasma exchange treatment.

22. The method according to claim 5, wherein the appropriate treatment is anti-tumor necrosis factor (TNF) monoclonal antibody treatment.

* * * * *